United States Patent [19]

Chlosta et al.

[11] Patent Number: 4,476,733
[45] Date of Patent: Oct. 16, 1984

[54] SAMPLER FOR FEEDING SAMPLES IN GAS CHROMATOGRAPHY

[75] Inventors: Wolfgang Chlosta; Peter Pospisil, both of Uberlingen, Fed. Rep. of Germany

[73] Assignee: Bodenseewerk Perkin-Elmer & Co., GmbH, Uberlingen, Fed. Rep. of Germany

[21] Appl. No.: 397,611

[22] Filed: Jul. 12, 1982

[30] Foreign Application Priority Data

Jul. 31, 1981 [DE] Fed. Rep. of Germany ....... 3130245

[51] Int. Cl.$^3$ ...................... G01N 35/04; G01N 35/06
[52] U.S. Cl. .................................... 73/863.91; 422/64; 422/65; 422/63; 73/863.11; 73/864.21; 73/864.91; 73/864.86; 73/863
[58] Field of Search ........... 73/864.21, 864.82, 864.81, 73/864.83, 864.84, 864.85, 864.86, 864.87, 863.91, 863.92, 863.11, 863.12, 863, 864.91; 422/63, 67

[56] References Cited

U.S. PATENT DOCUMENTS

| | | | |
|---|---|---|---|
| 3,333,648 | 8/1967 | Dodd | 73/863.92 X |
| 3,527,101 | 9/1970 | Sprunger et al. | 73/864.85 |
| 3,623,515 | 11/1971 | Gilson | 422/63 X |
| 3,917,455 | 11/1975 | Bak et al. | 422/64 |
| 4,011,048 | 3/1977 | Johnson, Jr. et al. | 422/63 |
| 4,077,444 | 3/1978 | Gilson et al. | 422/65 X |
| 4,237,733 | 12/1980 | Kolb et al. | 73/864.21 |
| 4,335,620 | 6/1982 | Adams | 73/863.11 |

FOREIGN PATENT DOCUMENTS

| | | |
|---|---|---|
| 1284660 | 9/1967 | Fed. Rep. of Germany . |
| 1297904 | 3/1970 | Fed. Rep. of Germany . |
| 1056762 | 1/1967 | United Kingdom ............ 73/863.91 |

Primary Examiner—Gerald Goldberg
Assistant Examiner—Tom Noland
Attorney, Agent, or Firm—F. L. Masselle; E. T. Grimes; R. A. Hays

[57] ABSTRACT

A plurality of samples subject to the same thermostatting time periods are directed one by one to the inlet section of a gas chromatograph for analysis in accordance with the head space method. To this end, a first heatable sample store adapted to be stepwise advanced is provided, in which thermostatting of the samples is accomplished. A second sample store also adapted to be stepwise advanced is provided, from which sample vessels are transferred one by one into the first sample store.

7 Claims, 18 Drawing Figures

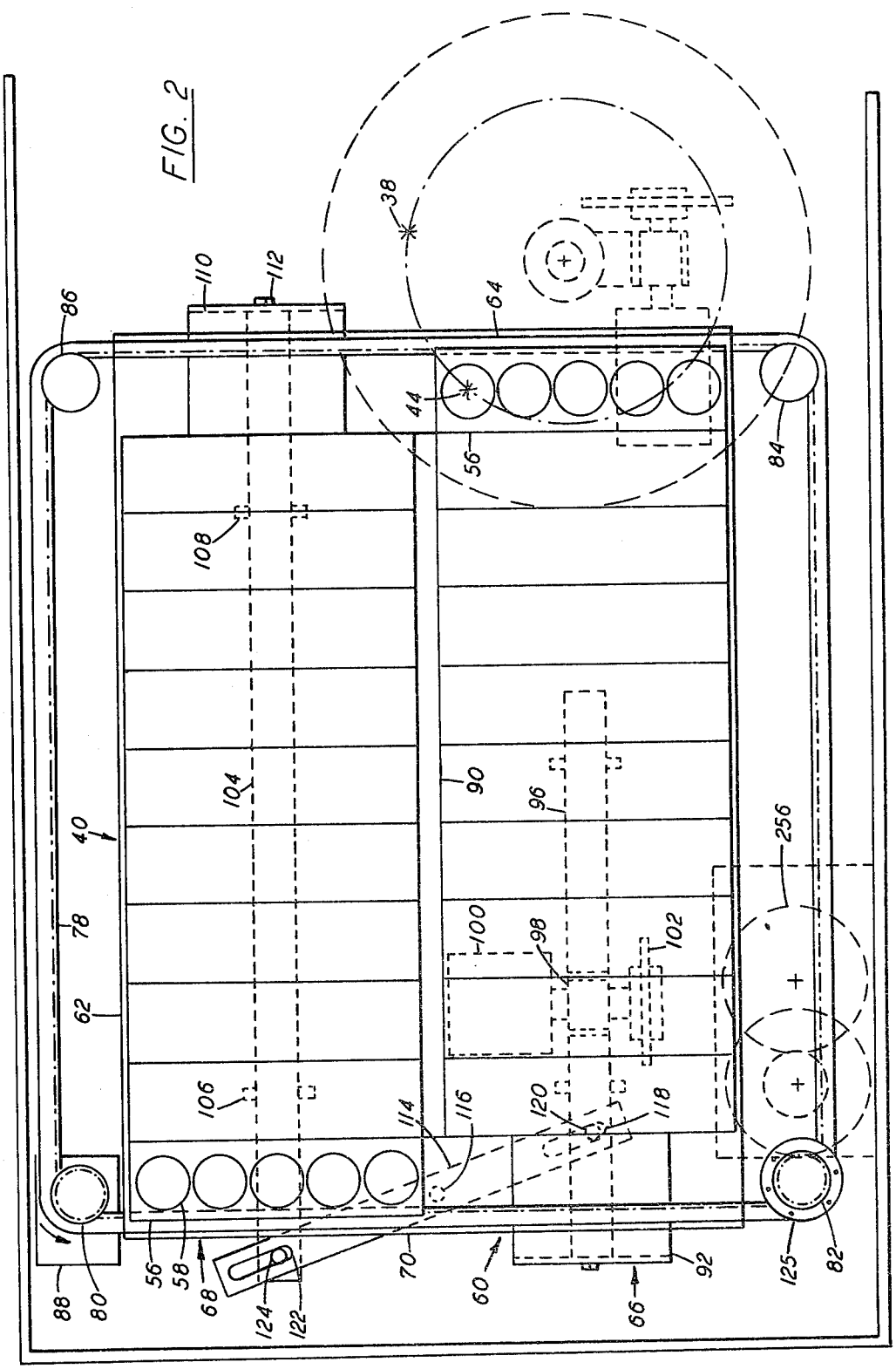

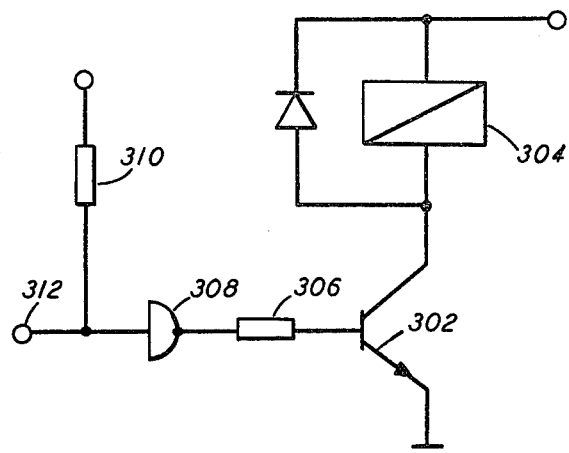
FIG. 16
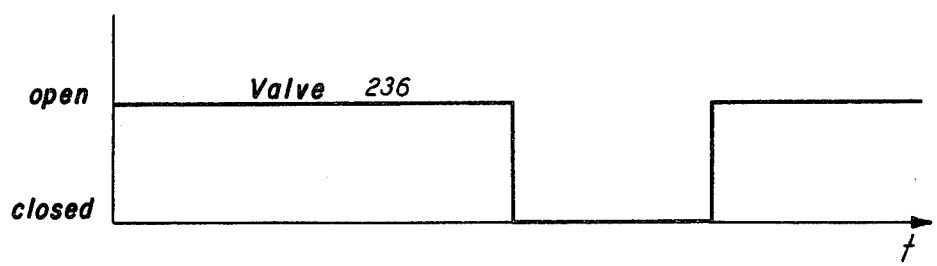
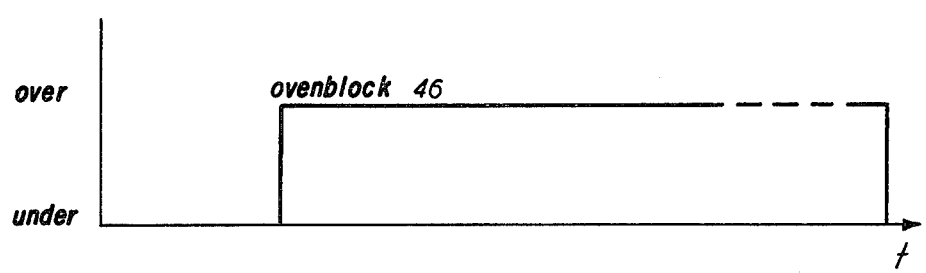
FIG. 17

SAMPLE FOR FEEDING SAMPLES IN GAS CHROMATOGRAPHY

BACKGROUND OF THE INVENTION

The present invention generally relates to a sampler mechanism for use in gas chromatography and, in particular, relates to a sampler mechanism adapted for use as a head space sampler wherein samples are automatically provided under comparable thermal conditions.

In a closed sample vessel, a state of equilibrium exists in the head space above a liquid sample wherein the partial pressures of the individual sample components are proportional to the concentrations thereof in the liquid sample. In a sampler operating on the head space method, a metered volume from the head space of the sample vessel is conveyed to the inlet of a gas chromatograph. The composition of the liquid sample in the sample vessel is thereafter derived from the analysis of the gas composition of the head space sample.

In one known sampler (German Pat. No. 1 284 660), sample vessels are sealed by a self-sealing diaphragm or septum. A sample is obtained by piercing the septum with a needle which is connected to the entrance of a gas chromatographic separating column. The entrance of the separating column is in turn connected to a carrier gas conduit, the flow of which is controlled by a solenoid valve. When the solenoid valve is open, the carrier gas pressure at the entrance of the separating column is transferred to the head space of the sample vessel via the needle which acts as a capillary such that an elevated pressure is built up therein. The partial pressures of the samples, however, are unaffected. The pressure at the entrance of the separating column breaks down when the carrier gas conduit is shut off. Thus, carrier gas plus sample vapor flow from the head space to the inlet of the gas chromatograph at the entrance of the separating column. The sample volume is determined by the time interval during which the solenoid valve is shut off.

To obtain reproducible results and sufficient vapor pressures, the sample vessels are usually controllably and reproducibly maintained at an elevated temperature. A variety of mechanisms have been developed for this purpose. For example, German Pat. No. 1 297 904 discusses such a sampler wherein a turntable having a liquid bath for receiving a plurality of sample vessels is arranged for being stepwise advanced. In this manner, the sample vessels are individually positioned below a stationary needle. Together with the liquid bath, the turntable is guided for vertical movement and is lifted to individually push sample vessels onto the needle to pierce the septum of the sample vessel.

In another design (German Offenlegungsschrift No. 2 818 251), a turntable consists of a stationary axle and a base plate. A metal block, heatable by an electric heater, serves as a thermostating means, which metal block is rotatably mounted about the stationary axle. The metal block having the axle as its center includes a circular array of axial through bores. A base plate closing the axial through bores from below has an aperture for pushing a sample vessel into one of the axial through bores aligned with the aperture. A cover, arranged to be pushed aside resiliently, is provided in front of the aperture.

In conventional samplers, sample vessels are manually set into a turntable and into the through bores of the rotatable metal block, respectively. Therefrom, the following problems result. It is possible to insert a plurality of sample vessels into the turntable and into the metal block, respectively, at a time. These samples might then automatically be sampled by means of an automatic control, through which the turntable may be stepwise advanced and may be lifted towards the needle. The number of the samples fed in this way is limited to the number of sample positions available in the turntable and in the metal block, respectively. Furthermore, the thermostating times for the different samples are different with this mode of operation. This can result in faulty measurements of samples in which thermal equilibrium is reached only very slowly and such a stationary state is not reached at the moment of the sample transfer. In this case, with different thermostating times, there are no comparable conditions for the different samples. It can also happen that samples chemically change due to the heating either by thermal decomposition or by reaction of their components with each other. In this case also, comparable conditions are not obtained if the thermostating times are different for the different samples. If this is to be avoided with conventional samplers, the samples must be supplied continuously at the same rate as the gas chromatographic analysis is carried out and the turn table is advanced.

SUMMARY OF THE INVENTION

Accordingly, it is one object of the present invention to provide a sampler mechanism that permits the automatic feeding of a large number of samples under comparable thermal conditions.

This object is achieved, at least in part, by providing a second sample vessel store arranged to be advanced stepwise, with means for transferring one sample vessel at a time from the second sample vessel store to a sample position to the first sample vessel store at a transfer station and means for synchronously controlling the first sample vessel store, the piercing and sample transfer means, the second sample vessel store and the sample vessel transfer means. Consequently, a larger number of samples may be inserted into the second sample vessel store arranged to be advanced stepwise. These sample vessels remain unheated. They are then automatically transferred to the first heatable sample vessel store and may there be heated during a constant thermostating time, until the sample is transferred to the inlet of the gas chromatograph.

Other objects and advantages will become apparent to one skilled in the art from the following detailed description and the accompanying drawing.

BRIEF DESCRIPTION OF THE DRAWINGS

An embodiment of the present invention will hereinafter be described in greater detail with reference to the accompanying drawing which is not drawn to scale and wherein:

FIG. 2 is a plan view of the sampler shown in FIG. 1;

FIG. 16 shows the control of one of the solenoid valves in the sample transfer means;

FIG. 17 illustrates the time history of the sample transfer; and

DETAILED DESCRIPTION OF THE INVENTION

Figure 1:
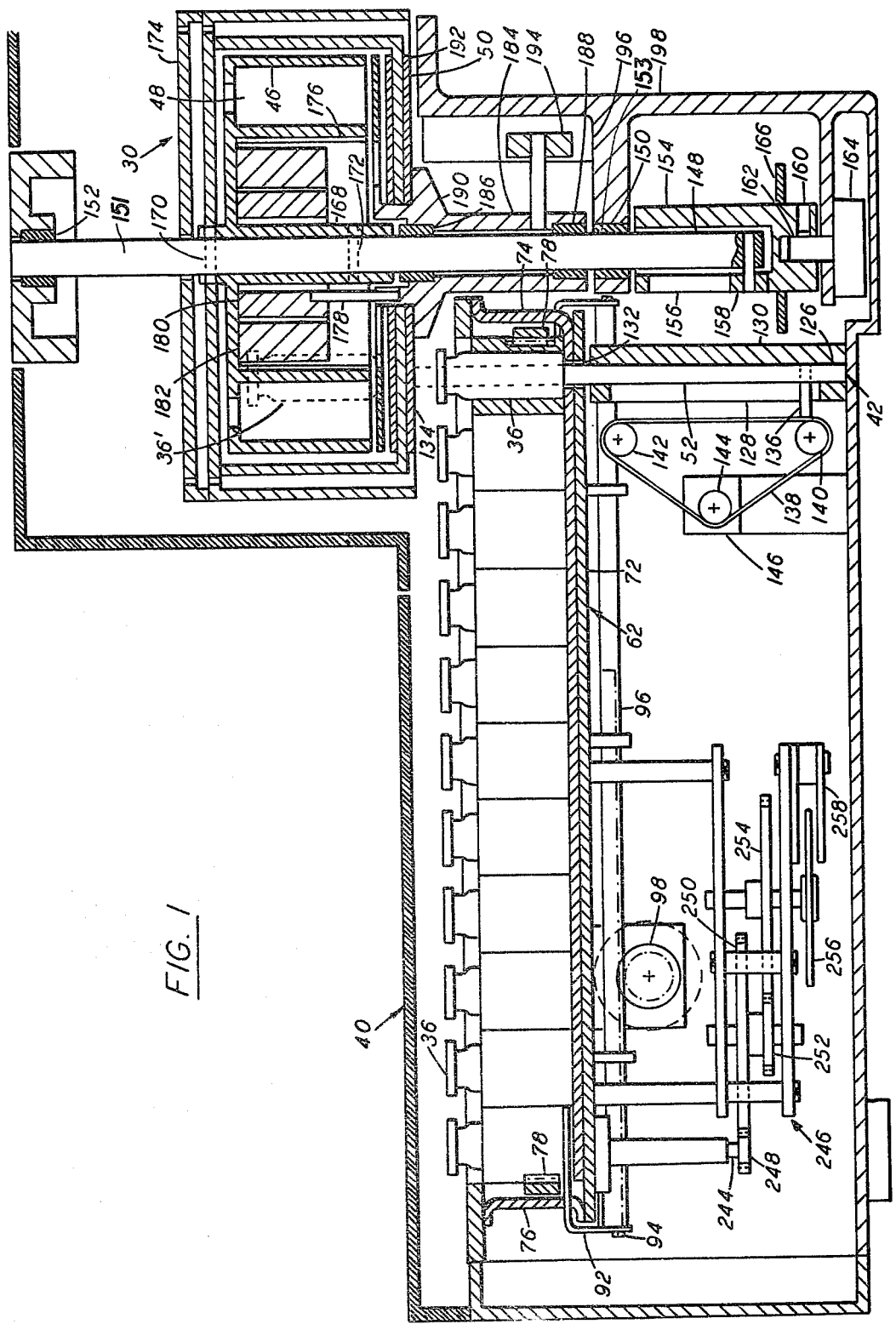
FIG. 1 is a schematic sectional view of a sampler embodying the principles of the present invention.

A sampler mechanism comprises a first heatable sample vessel store 30 arranged to be stepwise advanced including a plurality of sample positions, means 32 for piercing a needle 34 connected to the inlet part of a gas chromatograph (FIG. 3) through the closure members of the sample vessels 36 into head spaces formed above the samples in the sample vessels 36 at a sample station 38. Further, means are provided for transferring a volume of sample from the head space through the needle 34 into the inlet part of the gas chromatograph, which means are depicted in greater detail in FIG. 13.

Figure 13:
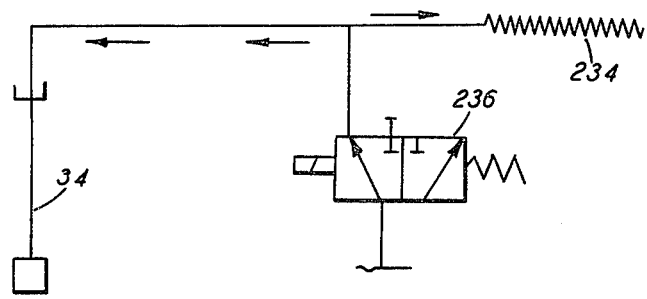
FIG. 13 shows a pneumatic circuit of the sample transfer means.

The sampler mechanism further includes a second sample vessel store 40 adapted to be advanced, means 42 for transferring a respective one of the sample vessels 36 at a time from the second sample vessel store 40 to a sample position of the first sample vessel store 30 at a transfer station 44 (FIG. 2) and means for a synchronized control of first sample vessel store 30, of piercing and sample transfer means 32 and FIG. 13, respectively of second sample vessel store 40, and of sample vessel transfer means 42.

The first heatable sample store includes a rotatably mounted heatable oven block 46 having a circular array of axial through bores 48 around the axis and a stationary base plate 50 having an aperture aligned with each of the through bores 48 at the transfer station 44. The sample transfer means 42 comprise a lifting member 52, which is arranged to push one sample vessel 36 at a time through the aperture into the through bore 42 aligned therewith. The needle 34 is affixed to the instrument at the sample station 38, and the piercing means 32 includes a lifting mechanism 54, which is adapted to lift the first sample vessel store 30 towards the needle 34.

The second sample vessel store 40 includes a plurality of elongated, generally block-shaped, sample holders 56, each of which is provided with an array of apertures 58 to receive sample vessels 36 and arranged as a column 60 on a table 62, with their longitudinal sides adjacent each other. On the side of the column 60 adjacent the transfer station 44, first conveying means 64 are provided, through which each of the sample holders 56 located on the end face of the column 60 may be stepwise advanced transverse to the column 60 such that the sample vessels retained in the sample holder 56 get to the transfer station 44 one after the other, and that eventually the sample holder 56 is laterally pushed out of the column. Second conveying means 66 are adapted to advance the sample holders 56 by one sample holder width in longitudinal direction of the column 60 after each lateral pushing out of the end face sample holder, such that the next sample holder 56 reaches the area of the first conveying means 64. Furthermore, the second sample vessel store 40 has a second column 68 of sample holders 56 extending parallel to the first column 60 on the table 62. Third conveying means are arranged to move the sample holder 56 on the end face of the second column 68 remote from the transfer station 44 (on the left hand side in FIG. 2) is transversely to the longitudinal direction of the second column 68 in front of the adjacent end face of first column 60, after the sample holders 56 of the first column 60 are advanced by one sample carrier width by means of the second conveying means 66. Fourth conveying means are provided to advance the sample holders 56 of the second column 68 by one sample holder width in a direction opposite to the second conveying means 66 after each lateral pushing out of the end face sample holder 56 from the second column 68 to the first column 60, and in a direction longitudinal of the second column 68 such that the next sample holder gets to the area of the third conveying means 70.

After the transfer of a sample vessel 36 from the sample holder 56 into the first sample vessel store 30, and after advancing the first sample vessel store 30, the sample vessel transfer means 42 transfers a sample vessel 36' located at the sample position within the first sample vessel store 30, which sample position, by the advancing, gets to the transfer station 44, from the first sample vessel store 30 to the vacant sample position of the second sample vessel store 40, that is, into the vacant aperture 58 of the sample holder 56.

The means for a synchronized control of the sample described below operates such that they leave all the samples in the first sample vessel store 30 for the same well-defined time between sample vessel transfer and sample transfer. In the event that the thermostating time T required for heating the sample is greater than the analysis time A required by the gas chromatograph and the analysis time A is greater than the clock interval $T_w$ between two subsequent steps of the first sample vessel store 30 arranged to be advanced stepwise, the sampler is controlled by the means for a synchronized control of the sampler in the following way. Only each i-th sample position is occupied by a sample vessel 36. In this case, $$i = 1 + INT\left(\frac{n \cdot A}{T}\right).$$

Where n is the number of the steps between transfer station 44 and sample station 38. INT means the integral part of the term in brackets. The analysis time between two subsequent sample transfers, Akorr, is given as $$A_{KORR} = \left(1 + INT\left(\frac{n \cdot A}{T}\right)\right) \cdot \frac{T}{n}.$$

If the thermostating time required for heating the sample is longer than the analysis time required by the gas chromatograph and the analysis time required by the gas chromatograph and the analysis time, in turn is smaller than the clock interval $T_w$, then each sample position of the first sample vessel store 30 arranged to be advanced stepwise is occupied by a sample by means of the means for a synchronized control of the sampler.

In case the thermostating time T required for heating a sample is smaller than the analysis time A required by the gas chromatograph, the means for a synchronized control of the sampler operate as follows:

There is only one sample at a time being transferred to the first sample vessel store 30. The sample vessel 36 transferred is advanced from the transfer position 44 by at least one step. After the termination of the thermostating time, the sample vessel 36 is advanced to the sample station 38. The sample transfer is started. After the termination of a time span corresponding to the difference (A−T) between analysis time and thermostating time, the transfer of a new sample vessel from the second sample vessel store 50 to the first sample vessel store 30 and the discharge of the sample vessel treated previously is effected. The different units of the sampler are described in detail hereinbelow.

The table 62 of the second sample vessel store 40 comprises a plate 72. A trough-like sheet-metal part 74 is mounted on the plate 72 which sheet metal part is open on its left hand side as shown in FIG. 1. There, the "trough" formed by sheet metal part 74 is closed by means of a sheet metal part 76. As can be seen from FIG. 2, two columns 60 and 68 of sample holders 56 having five apertures 58 each are located on table 62. The first and third conveying means 64 and 70, respectively, include opposite portions of an endless tooth belt 78 guided along a rectangle around a driving tooth belt pulley 80 and tooth belt pulleys 82, 84 and 86. The driving tooth belt pulley 80 is affixed to the shaft of a servomotor 88. The servomotor 88 is adapted to drive tooth belt pulley 80 in the direction of the arrow such that tooth belt 78 is moved counter clockwise. The sample holders 56 are provided with teeth along their longitudinal sides, which teeth engage tooth belt 78 when one of the sample holders 56 is pressed thereagainst. As shown in FIG. 1, tooth belt 78 is guided on the left hand and right hand sides in FIGS. 1 and 2 on the inner side of the trough 74 and of the sheet metal part 76, respectively, whereas, on the upper and lower sides in FIG. 2, it is passed out of the trough and extends outside it. Inside the trough which is divided into two partial chambers by means of a partition 90, the sample holders 56 are movably guided between the edges of the trough-like sheet metal part 74 and the partition 90 in two columns 60 and 68, as said before. The second conveying means 66 has an L-shaped sheet metal bracket 92 extending, with its horizontal leg, in front of the end face of the first column 60 of the sample holders 56 underneath the tooth belt 78 through an aperture of sheet metal part 76 into the trough. With its vertical leg, sheet metal bracket 92 is mounted on a rack 96 by means of a screw 94. Rack 96 is rectilinearly guided on the bottom side of table 62 and meshes with a pinion 98 driven by a servomotor 100. A signal disc 102 is located on the shaft of servomotor 100 and pinion 98, which signal disc is arranged to generate a signal, when pinion 98 and, thus, rack 96 have obtained their final positions.

Figure 8:
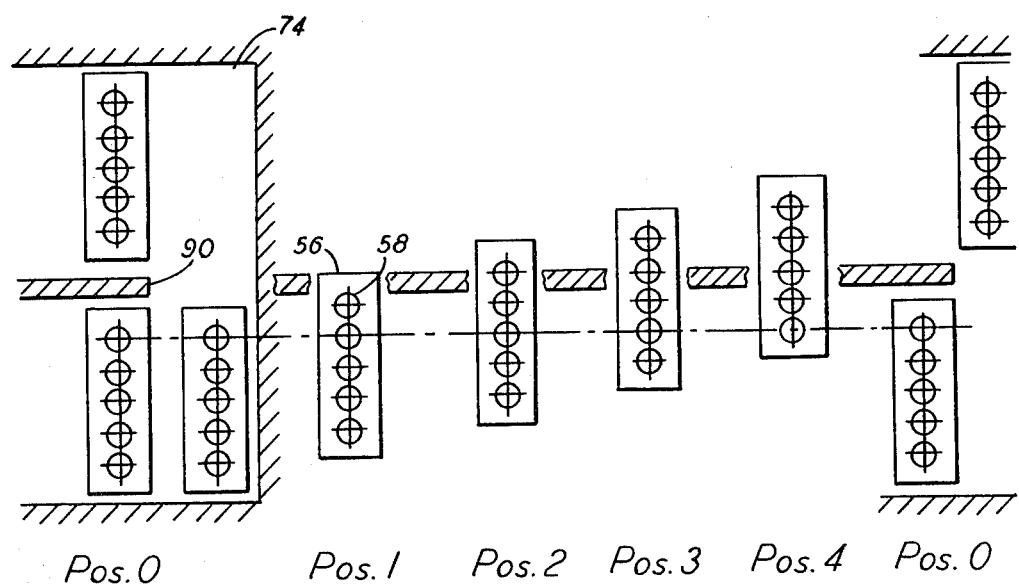
FIG. 8 illustrates a time diagram of the stepwise movement of the sample carriers towards the transfer station.

The third conveying means includes a pusher 104, which is guided on the bottom side of table 62 through guides 106 and 108. An L-shaped sheet metal bracket 110 is affixed to the pusher 104 by means of a screw 112. With its horizontal leg, sheet metal bracket 110 extends through an aperture of sheet metal part 74 in front of the right hand end faces, in the figures, of column 68 and underneath tooth belt 78. With a movement of pusher 104 to the left hand side in FIG. 2, column 68 may be moved to the left hand side, until the sample holder 56 forming the left end face of column 68 engages tooth belt 78. Rack 96 and pusher 104 are coupled by means of a link 114. Link 114 is pivotable about a pivot axis 116 and, on one end, engages rack 96 by means of an oblong hole 122 and a pin 124. With a movement of the rack 96 to the right hand side in FIG. 2, pusher 104, in same manner, is moved to the left hand side in FIG. 2. Thus, the next sample carrier 56 out of the area of column 60 is moved to the right hand side to engage tooth belt 78, after the stepwise movement of the sample carrier 56 on the right end face of column 60. After the sample carrier 56 on the left hand face of column 68 has been moved downwards into the area of column 60 by means of tooth belt 78, column 68, is simultaneously moved to the left hand side, and the next sample carrier is caused to engage tooth belt 78 again. Thus, the right part of tooth belt 78, in FIG. 2, forms the "first conveying means", through which the end face sample carrier of column 60 is stepwise moved upwards. The left part of tooth belt 78, in FIG. 2, forms the "third conveying means", through which the left end face sample carrier 66 is stepwise moved downwards from column 68 to column 60. As illustrated in FIG. 8, the apertures of the right end face sample carrier 56 of column 60 are moved one after the other to the transfer station 44 with this movement.

Figure 12:
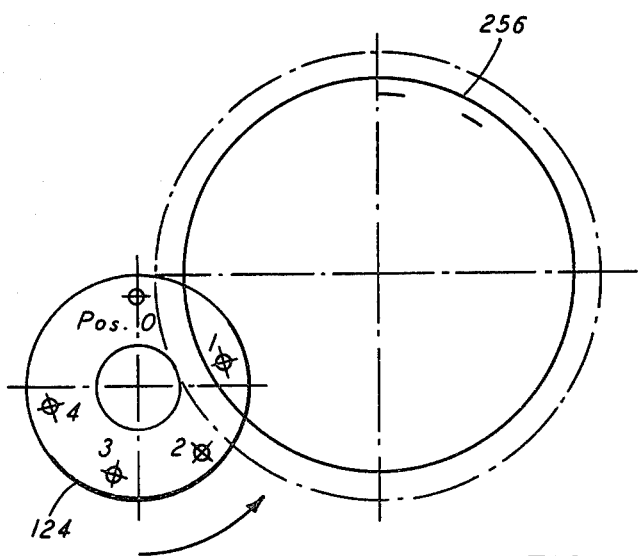
FIG. 12 schematically shows the generation of the positioning signals for the movement of the first conveying means, and of the signals for the identification of the samples.

A signal disc 125 is connected to the tooth belt pulley 82. As can be seen best from FIG. 12, signal disc 125 has five holes designated by "0", "1", "2", "3" and "4". The holes are detected by a photoelectric light barrier (not shown). In a preferred embodiment, each distance between the sample vessels in the sample holder is 26 mm. The distance between the holes "0" and "4" is selected such that, with each rotary motion of signal disc 125 and thus of tooth belt pulley 82 from one hole to the next one, a movement of tooth belt 78 and thus a displacement by 26 mm of the right sample holder of column 60 and of the left sample holder of column 68 is achieved. The distance between hole "4" and hole "0" is chosen such that, with a complete revolution of tooth belt pulley 82, each of the two sample holders is moved by 140 mm and thus into the other column 68 and 60, respectively. In the preferred embodiment, tooth belt 78 has a graduation of 10 mm. Tooth belt pulley 82 has 14 teeth such that one revolution corresponds with a transport distance of 140 mm.

Figure 9:
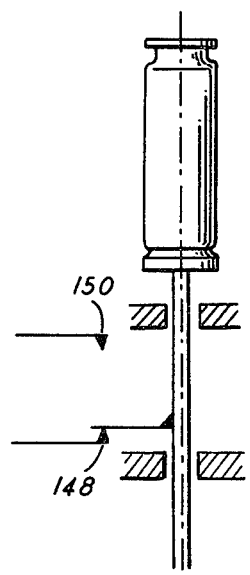
FIG. 9 schematically shows the sample vessel transfer means for transferring a sample vessel from the sample holder into the first sample vessel store.

The sample vessel transport means 42 as lifting member 52 includes a push rod 126 which is slidingly guided within a sleeve 130 provided with a longitudinal slot 128. The push rod 126 is aligned with an aperture 132 of table 62, with one of the apertures 58 of a sample holder 56, and with the aperture 134 in the stationary base plate of sample vessel store 30. Push rod 126 is connected to a chain 138 by means of a pin 136. Chain 138 is guided in parallel to push rod 126 and sleeve 130 over two sprocket wheels 140 and 142. Furthermore, chain 138 is guided over a sprocket wheel 144 arranged to be driven by a servomotor 146. As can be seen from FIG. 9, end switches 148 and 150 are provided to produce a signal, when push rod 126 has reached its bottom or top final position, respectively.

The first sample vessel store 30 having rotatable oven block 46 is positioned on a shaft 151. Shaft 151 is guided for rotary and longitudinal movement in bearings 152 and 153. The bottom end of shaft 151 is guided for movement in longitudinal direction within a sleeve 154. Sleeve 154 includes a longitudinal slot 156, in which a ball bearing roller 158 mounted on shaft 151 is guided. Thus, shaft 151 is non-rotatably retained relative to sleeve 154, but movable in longitudinal direction. Sleeve 154 is connected to the shaft 162 of a servomotor 164 by means of a set screw. Therefore, servomotor 164 may rotate shaft 151 and so oven block 46. Simultaneously, an axial movement, to the top and to the bottom in FIG. 1, of oven block 46 and shaft 151 is possible. The movement of oven block 46 is monitored by a signal disc 166 disposed on sleeve 154 and interacting with a light barrier (not shown).

Oven block 46 is secured to shaft 151 via a hub 168 by means of transverse pins 170 and 172. It is surrounded by an insulating sheath 174. The stationary base plate 50 is located between oven block 46 and insulating sheath 174. The insulating sheath has an aperture aligned with aperture 134 in the base plate 50. A heater 176 is disposed within the through bores 48 in the oven block, which heater is supplied with current by means of a stationary conductor 178 and slip rings 180 and 182. Insulating sheath 174 and base plate 50 are connected to a sleeve 184 mounted on shaft 151 through bearings and engaging the bottom side of a plate 192 carrying the insulating sheath 174 by means of a flange 190. Sleeve 184 carries a lateral roller 194 formed by a ball bearing and guided within a groove 196 of a housing 198. Thereby, sleeve 184 retained against rotation, but is movable in vertical direction.

Figure 4:
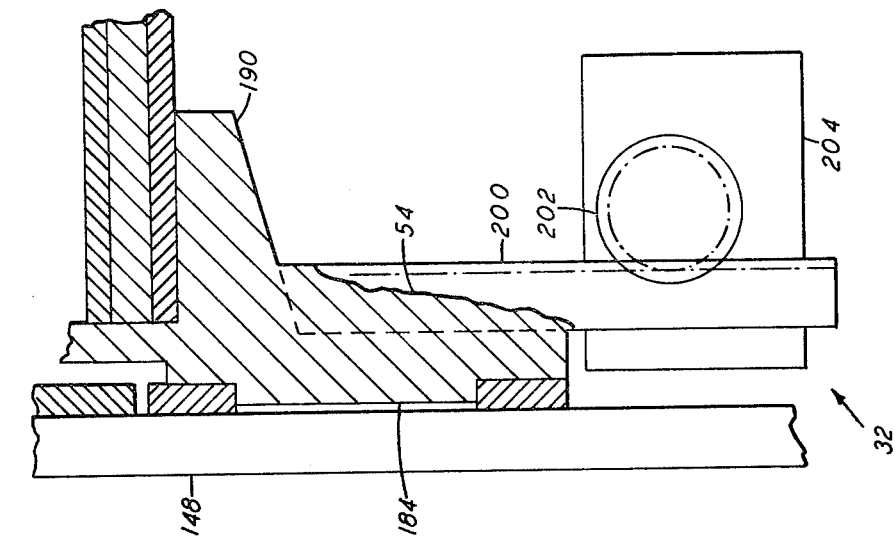
FIG. 4 is a partial sectional view showing a motor and mechanism for lifting the first sample vessel store towards the needle.
Figure 11:
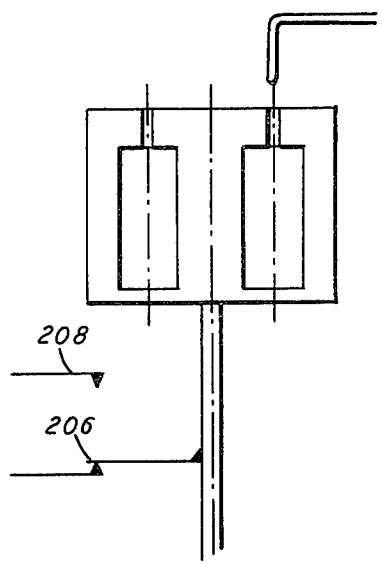
FIG. 11 schematically shows the movement of the first sample vessel store towards the needle.

As can be seen from FIG. 4, a rack 200 is provided on the flange 190 and on the sleeve 184, which flange extends vertically with respect to shaft 151. Rack 200 engages a pinion 202 arranged to be driven by a servomotor 204. Thus, the sleeve 184 and, together with it, insulating sheath 174, oven block 46 and shaft 151 connected thereto are movable from the position illustrated up towards the needle 34 by means of the servomotor 204. As schematically illustrated in FIG. 11, the lifting movement is monitored by sensors 206 and 208.

Figure 3:
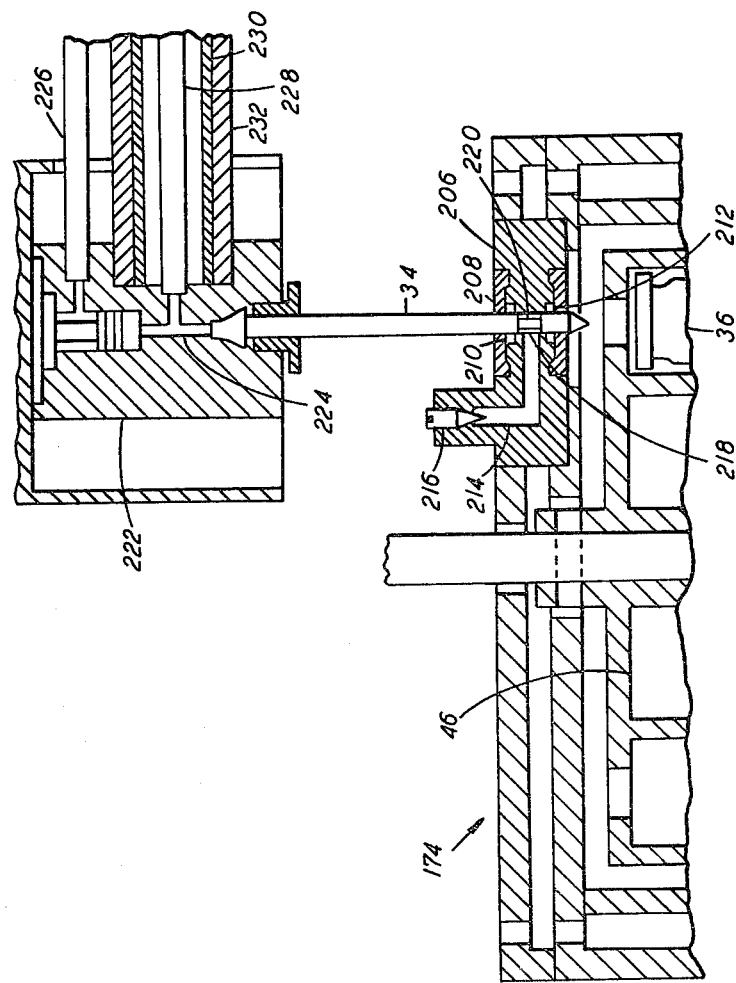
FIG. 3 is a partial sectional view of the upper part of the heated first sample vessel store.

FIG. 3 shows the needle 34 with the stationary insulating sheath 174 and the oven block 46 in a partial view. Insulating sheath 174 and oven block 46 are located in their bottom positions, as illustrated in FIG. 1 as well. A housing 206 is incorporated in the insulating sheath 174, which housing has a housing bore 208. The needle is sealingly guided within this housing bore 208. Sealing is achieved by two O-rings 210 and 212. A lateral outlet passage 214 branches off from housing bore 208, which outlet passage is connected to atmosphere through a restrictor in the form of an adjustable needle valve 216. Needle 34 includes a circumferential groove 218, into which the lateral exit aperture 220 of the needle opens. In the position of rest illustrated, the circumferential groove 218 having exit aperture 220 is connected to the outlet passage.

One example of a preferred needle assembly is described in U.S. patent application Ser. No. 354,409, filed Mar. 3, 1982 (corresponding to West German patent application No. P31 09 616.6 filed in West Germany on Mar. 12, 1981) and assigned to the assignee hereof, which description is incorporated by reference herein.

If insulating sheath 174 and oven block 46 are lifted, housing 206 having housing bore 208 is moved upwards on the needle 34. Needle 34 pierces the septum sealing the sample vessel 36, until the lateral exit aperture 220 of needle 34 is located in the head space of sample vessel 36.

The needle is mounted on a block 222 containing a passage 224. Passage 224 communicates with needle 34. A carrier gas conduit 226 opens into passage 224. A conduit 228 branches off from passage 224, which conduit leads to the inlet part proper of the gas chromatograph and to the entrance of the separating column. Conduit 228 is heated by a heater 230 and surrounded by an insulating coating 232.

FIG. 13 shows the pneumatic circuit of the sample transfer means.

Needle 34 is connected to the entrance of a separating column 234. A predetermined carrier gas pressure is supplied to the entrance of separating column 234 through a solenoid valve 236.

Figure 5:
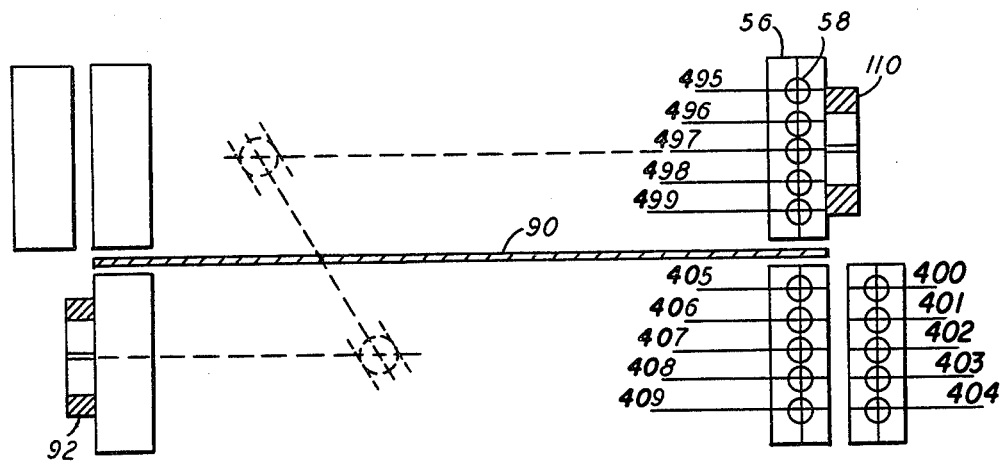
FIG. 5 illustrates schematically the numbering of the samples and the advancing towards the transfer station, effected by first conveying means, of a respective one of the sample holders with its different sample vessels.

A code disc 256 is connected to the tooth belt pulley 82, the shaft of which is designated by 244, by means of a gear unit 246 consisting of gears 248, 250, 252 and 254. The code disc 256 is driven by tooth belt pulley 82 with a step-down ratio of 1:20. The code disc is photoelectrically readout by means of a light barrier arrangement 258 and contains codes for one hundred different samples. FIG. 5 shows, in what way the individual apertures 58 of the sample holders are designated from "400" to "499".

Figure 6:
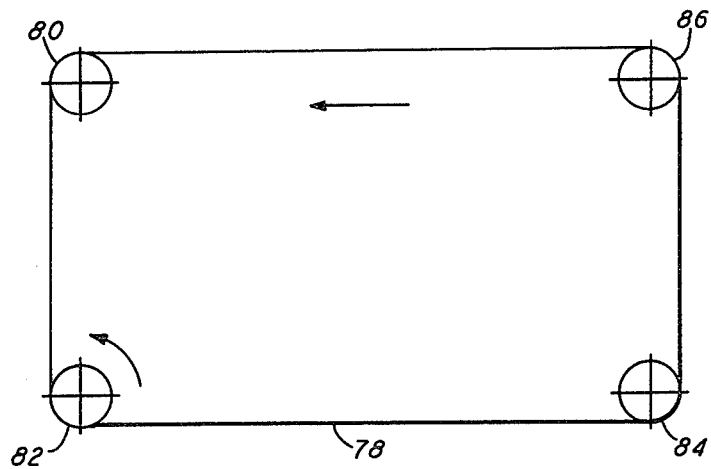
FIG. 6 illustrates schematically the conveying means.
Figure 7:
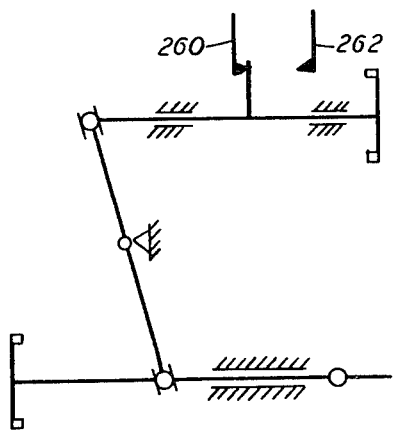
FIG. 7 illustrates the advancing of the sample holders arranged in two columns in longitudinal direction of the columns, effected by second conveying means.
Figure 10:
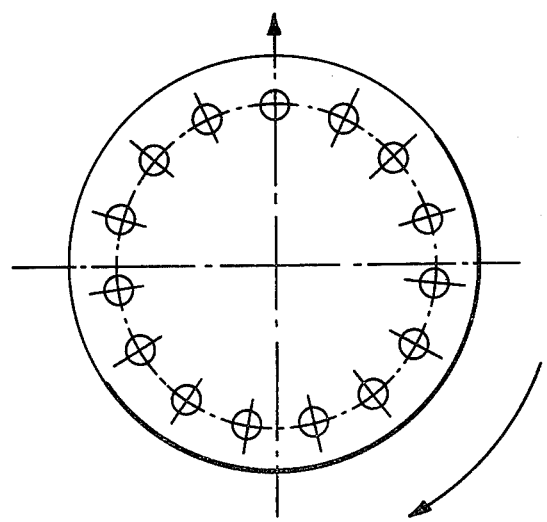
FIG. 10 schematically shows the stepwise movement of the sample vessels in the first sample vessel store.

A series of movements is carried out in the sampler, which movements are preferably controlled by individual actuators. The sample holders 56 are moved transverse to the longitudinal direction of the columns upwards on the right end of column 60 (FIG. 2) and downwards on the left side of column 68 by tooth belt 78. Servomotor 88 is the servomotor for this movement. FIG. 6 shows this movement in detail. The pushers, formed by the sheet metal brackets 92 and 110, arranged to push the sample holders 56 in longitudinal direction of columns 60 and 58, respectively, make a return stroke each permitting the transverse movement of the sample holders 56 from the right end of column 60 up to column 68 and from the left end of column 68 down to column 60, and then a forward stroke, wherein sheet metal bracket 92 moves to the right in FIG. 2, and sheet metal bracket 110 moves to the left. These two movements monitored by signal disc 102 are initiated by servomotor 100. In FIG. 7, these movements are illustrated in detail, the function of the signal disc 102 being symbolized by end switches 260 and 262. Other movements are the up and down movement of the push rod 126, through which movement a sample vessel 36 is introduced into the oven block 46, and, after a rotation of the oven block, another sample vessel may be let down from the oven block, if desired. These movements monitored by the end switches 148 and 150 are controlled by servomotor 46. This is shown separately in FIG. 9. The movement illustrated in FIG. 10, namely the rotation of the oven block 46, is controlled by servomotor 164 and monitored by a signal from signal disc 166. Finally, FIG. 11 schematically illustrates the movement of the first sample vessel store 30 towards the needle 34, which movement is initiated by servomotor 204 and monitored by sensors 206 and 208 (FIG. 11). Finally, the solenoid valve 236 forming a part of the "sample transfer means is provided as an actuator".

Figure 18:
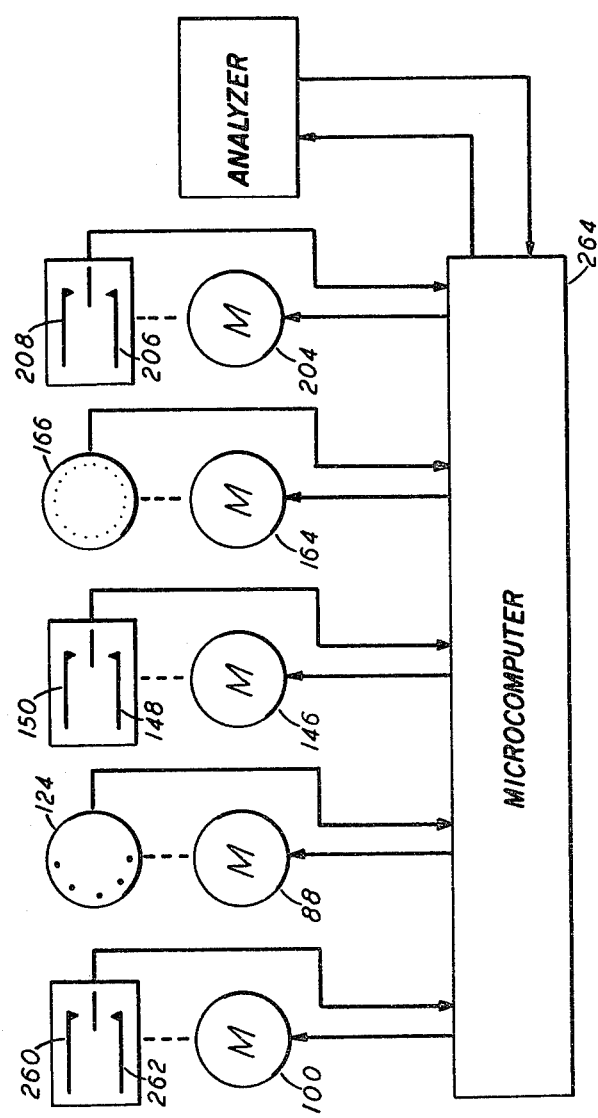
FIG. 18 is a block diagram of a synchronized control of the individual components of the sampler and the associated servomotors and solenoid valves.

A microcomputer can be provided as the "means for a synchronized control" of the single components of the sampler, which microcomputer controls the servomotors and the solenoid valves, and, on the other hand, receive feedback signals from the different above-mentioned sensors. This is illustrated schematically in the block diagram of FIG. 18.

Figure 14:
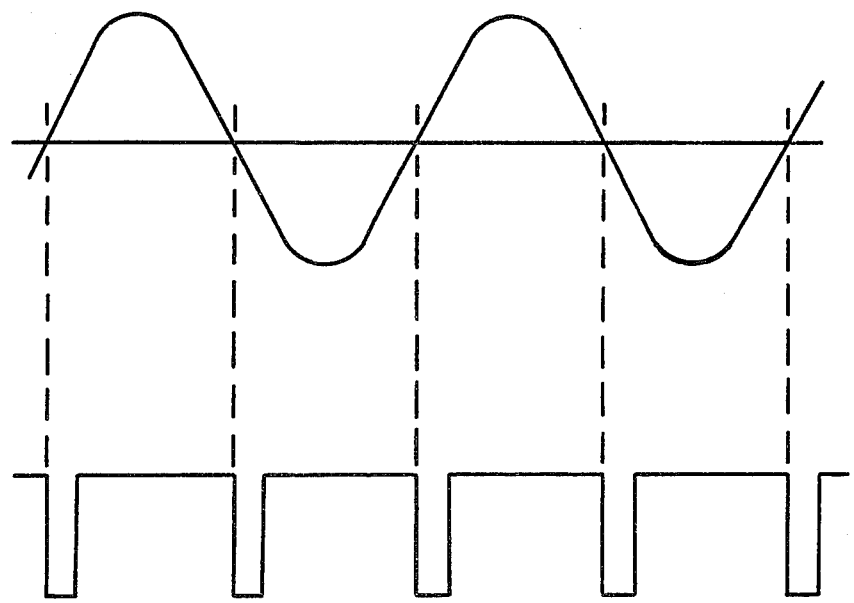
FIG. 14 illustrates the generation of clock pulses for the control of the servomotors.

FIG. 14 illustrates the generation of clock pulses having twice the main frequency. These clock pulses are used for controlling the synchronous motors and the heaters such that the motors and heaters are switched with zero passage of the main voltage and thus interference peaks are avoided, which might lead to faulty operation of the microcomputer.

Figure 15:
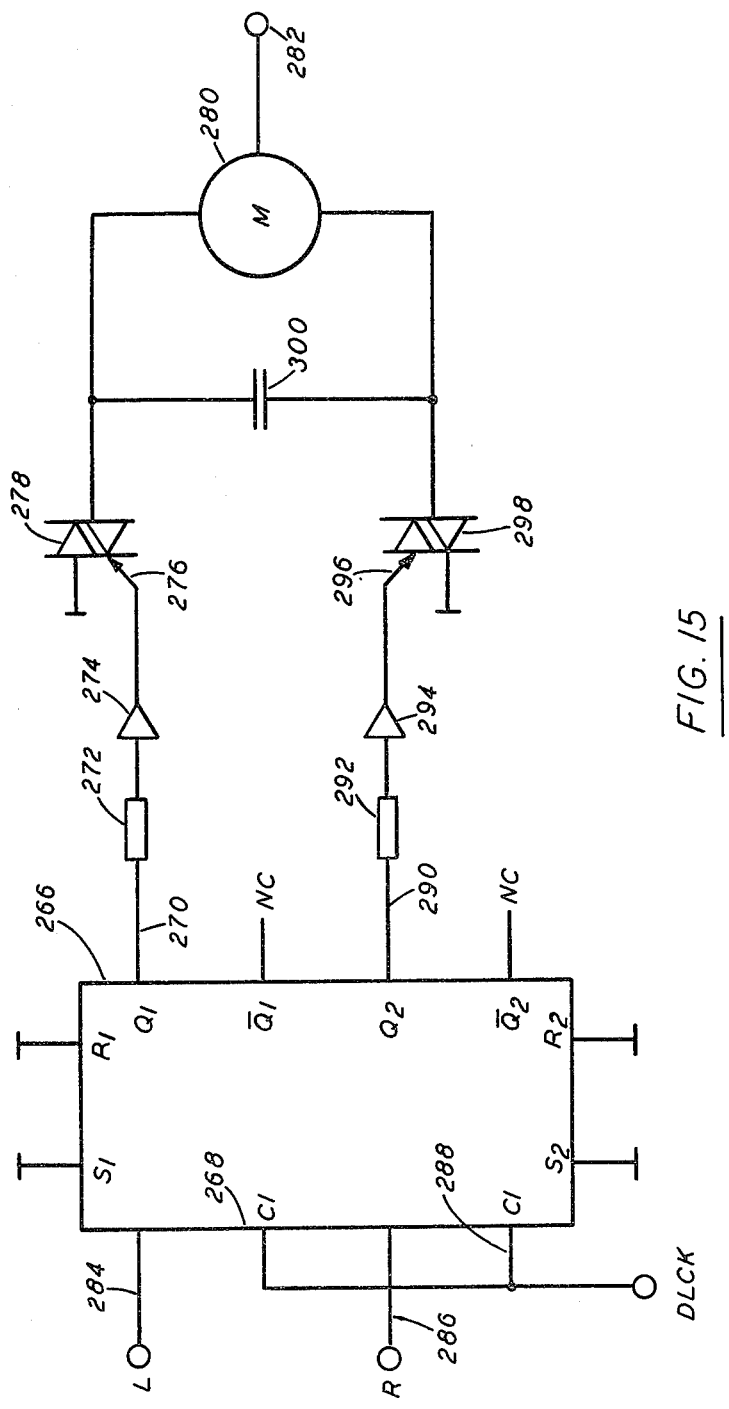
FIG. 15 is a wiring diagram and shows the control of one of the servomotors.

The motor control is illustrated in FIG. 15.

A switch-on signal given by the microcomputer 264 is applied to a D-flip-flop 266, the clock input 268 of which receives the clock pulses from the clock input, DLCK, synchronized with the main frequency according to FIG. 14. Then, at the Q output 270, a switch-on signal appears, the front slope of which coincides with one of the clock pulses. This switch-on signal is applied to the gate 276 of a triac 278 through a resistor 272 and a diode 274, through which triac the circuit of the servomotor 280 designed as a synchronous motor is completed, which servomotor is applied to a 24 volt. a.c. voltage by means of a terminal 282.

In FIG. 15, flip-flop 266 is a double-D flip-flop having an input 284 for counter-clockwise rotation and an input 286 for clockwise rotation, wherein the latter interacts with a clock input 288 to which the clock pulses according to FIG. 14 are applied as well. With a switch-on signal applied at the input 286, an output signal synchronized with one of the clock pulses appears at a Q-output 290, which output signal is applied to the gate 296 of a triac 298 through a resistor 292 and a diode 294. The circuit of motor 280 for reverse rotation is completed through triac 298. Numeral 300 designates a starting capacitor.

In similar manner known by those skilled in the art and therefore not illustrated, the solenoid valve can be controlled through a transistor 302, the emitter-collector junction of which being in series with the coil 304 of the solenoid valve is connected to a voltage of +24 volt. The base of transistor 302 is connected to the output of an inverter 308 through a resistor 306, to the input of which inverter a voltage of +15 volt is applied through a resistor 310. The transistor 302 is rendered conductive by an L-signal from the microcomputer being applied to the input of inverter 308 through a terminal 312, whereby the solenoid valve is energized.

FIG. 17 shows the time history of the operation of the solenoid valve in its relation to the lifting movement of the first heatable sample vessel store 30.

The operation of the device described is as follows:

Starting from a state in which the right sample holder 56 of the column 60 engages the tooth belt 78 and the left sample holder of the column 68 also engages the tooth belt 78, the tooth belt 78 is stepwise advanced by the servomotor 88, the individual steps being monitored by the signal disc 125. Thereby, the different apertures of the right sample holder 56 of column 60 are one by one moved into the transfer position 44, as illustrated in FIG. 8, the servomotor 146 is switched on and moves the push rod 126 upwards such that it pushes the sample vessel 36 disposed in the respective aperture 58 upwards into a through bore 48 of the oven block 46. The oven block 46 is advanced by the servomotor 164. Afterwards, the servomotor 146 again moves the push rod 126 downwards. Thereby, another sample vessel having reached the transfer station due to the advancing may fall down together with the push rod 126 and may get into the now vacant aperture 58 of the sample holder 56, if desired. After the sample has been thermostatted in the oven block 46 for a predetermined time, the first heated sample vessel store 30 is lifted by the servomotor 204 together with the oven block 46 and the insulating sheath 174 such that the needle 34 is caused to pierce the septum sealing the sample vessel 36. The carrier gas pressure being effective over the open solenoid valve 236 is transferred to the closed sample vessel. Subsequently, the solenoid valve 236 is closed for a predetermined time. Thereby, the carrier gas pressure at the entrance of the separating column 234 breaks down, and a well-defined gas flow out of the head space of the sample vessel 36 through the needle 34 to the separating column 234 is caused. Then, the first sample vessel store 30 is again lowered into the position illustrated in FIG. 3 by the servomotor 204. The solenoid valve 236 is again lowered down into the position depicted in FIG. 3 opened again. Thereby, the sample sucked into the entrance of the separating column is transported through the separation column 234. Simultaneously, a restricted carrier gas flow flows off through the needle 34 and the needle valve 216, whereby the needle 34 is flushed by carrier gas.

What is claimed is:

1. A sampler for sequentially feeding samples from a sample vessel head space to an inlet of a gas chromatograph; said sampler comprising:
a first heatable sample vessel store having a plurality of sample positions, said store being adapted for stepwise advancement and including a rotatably mounted heatable oven block having a circular array of axial throughbores around the rotational axis of said block and a stationary base plate having an aperture alignable with each of said throughbores at a transfer station;
a second sample vessel store adapted for stepwise advancement;
means for transferring one sample vessel at a time from said second store to one of said sample positions in said first sample store, said transfer occurring at said transfer station;
means for advancing said sample vessel from said transfer station to a sampling station;
means for causing a needle to penetrate into said head space of said sample vessel whereby a head space sample can be transferred to said inlet; and
means for synchronously controlling said first store, said second store, said sample vessel transfer means and said needle penetration of said sample vessel.

2. Sampler as claimed in claim 1, wherein said sample transfer means comprises a lifting member arranged to push one sample vessel at a time through said aperture of said stationary base plate into the throughbore of said first heatable sample vessel store aligned therewith.

3. Sampler as claimed in claim 1 or 2, wherein:
said needle is stationary at said sample station; and
said piercing means includes a lifting mechanism which is adapted to lift said first sample vessel store towards said needle.

4. Sampler as claimed in claim 3 wherein:
said second sample vessel store comprises a plurality of elongated, generally block-shaped sample holders, each said holder being provided with an array of apertures to receive sample vessels therein, said holders being arranged as a column on a table with their longitudinal sides adjacent each other;
first conveying means on one side of said column adjacent said transfer station for transversely, with respect to said column, conveying whereby, each respective sample holder located at one end face of said column is stepwisely advanced and whereby said sample vessels retained in said sample holder reach said transfer station one after the other, and that eventually said sample holder is transversely ejected from said column; and
second conveying means for advancing said sample holders by one sample holder width in longitudinal direction of said column after each said end face located sample holder is ejected such that the next sample holder reaches said first conveying means.

5. Sampler as claimed in claim 4, wherein said second sample vessel store further includes a second column of sample holders extending parallel to said first column on said table as well as third conveying means for moving said sample holder positioned at the end face of said second column remote from said transfer station transversely with respect to the longitudinal direction of said second column behind the adjacent end face of said first column, after said sample holders of said first column have been advanced by one sample holder width by means of said second conveying means; and
fourth conveying means for advancing said sample holders of said second column one sample holder width in a direction opposite to said conveying direction of said second conveying means after each transverse movement of said end face positioned sample holder from said second column to behind said adjacent end face of said first column whereby said sample holders so moved each consecutively reach the region of said third conveying means.

6. Sampler as claimed in claim 5, wherein after the transfer of said sample vessel from said sample holder into said first sample vessel store and after said stepwise advancement of said first sample vessel store, said sample vessel transfer means transfers a sampled sample vessel from a sample location in said first sample vessel store to a vacant sample position in said second sample vessel store after said sampled sample vessel reaches said transfer station upon further stepwise advancement of said first sample vessel store.

7. Sampler as claimed in claim 6, wherein said means for synchronized control of said sampler maintains all said sample vessels for the same preselected time between said sample vessel transfer into and transferring said sample vessel from said first heated sample vessel store.

* * * * *